United States Patent
Meurer

(10) Patent No.: US 7,528,949 B2
(45) Date of Patent: May 5, 2009

(54) AERIAL-SUPPORTED PROCEDURE FOR EXPLORATION OF HYDROCARBON DEPOSITS

(76) Inventor: Heinrich Meurer, Lessingstr, 30, D-50321 Bruchl (DE)

( * ) Notice: Subject to any disclaimer, the term of this patent is extended or adjusted under 35 U.S.C. 154(b) by 86 days.

(21) Appl. No.: 11/839,191

(22) Filed: Aug. 15, 2007

(65) Prior Publication Data
US 2009/0045327 A1 Feb. 19, 2009

(51) Int. Cl.
*G01J 3/30* (2006.01)
(52) U.S. Cl. .................................... 356/317; 250/253
(58) Field of Classification Search ................. 356/300, 356/317, 445; 250/253; 435/29
See application file for complete search history.

(56) References Cited

U.S. PATENT DOCUMENTS

| 2,777,799 A | | 1/1957 | Davis | |
|---|---|---|---|---|
| 3,985,619 A | * | 10/1976 | Barringer | ........................ 435/9 |

FOREIGN PATENT DOCUMENTS

| DE | 4126692 | 2/1993 |
|---|---|---|
| WO | 97/03201 | 1/1997 |
| WO | 02/068473 | 9/2002 |
| WO | 99/34212 | 9/2008 |

OTHER PUBLICATIONS

Laserscanner ALTM 3100 of the firm Optech, Canada, Copyright 2004, Optech Incorporation.
Litemapper 2800 of the IGI mbH, Germany; Oct./Nov. 2006; GEOinformatics.
Marianne M. Figueira et al.; Production of Green Fluorescent Protein by the Methylotrophic Bacterium Methylobacterium Extorquens; FEMS Microbiology Letters; 2000; pp. 195-200; 193; Elsevier Science B. V.
Robert M. De Lorimier et al.; Construction of a Fluorescent Biosensor Family; Protein Science; 2002; pp. 2655-2675; 11; Cold Spring Harbor Laboratory Press.
Jay Rauschkolb; Using GIS and Satellite Imagery to Locate Hydrocarbons; Presented at the ESRI International Use Conference in San Diego,I CA; Jul. 2-10, 2003; Paper #868; USA.
N.A. Sorkhoh et al.; Establishment of oil-degrading bacteria associated with cyanobacteria in oil-polluted soil; Journal of Applied Bacteriology; 1995; pp. 194-199.
Dieter Schumacher; Managing Exploration Risks: Lessons Learned from Surface Geochemical Surveys and Post-Survey Drilling Results; Oral presentation at AAPG Convention in Houston, TX and CSPG in Calgary; 2002.
Manfred Wagner et al.; Mikrobielle Prospektion Auf Erdol Und Erdgas in Ostdeutschland; Geol. Jb; 1998; pp. 287-309; A149; Germany (Abstract Only).
Manfred Wagner et al.; Case Histories of Microbial Prospection for Oil and Gase, Onshore and Offshore in Northwest Europe; AAPG Studies in Geology No. 48 and SEG Geophysical References Series No. 11; 2002; pp. 453-479.
Dieter Schumacher; Hydrocarbon-Induced Alteration of Soils and Sediments; Hydrocarbon migration and its near-surface expression: AAPG Memoir 66; 1996; pp. 71-89.

* cited by examiner

*Primary Examiner*—Kara E Geisel
*Assistant Examiner*—Abdullahi Nur
(74) *Attorney, Agent, or Firm*—Marianne Fuierer; Moore & Van Allen PLLC

(57) ABSTRACT

The present invention refers to an aerial-supported procedure for the exploration of hydrocarbon deposits, especially crude oil and gas deposits, using fluorescence procedures, including aerial-supported geo-referencing of the detected locations by means of a digital terrain model, employing biosensors which are sensitive to hydrocarbons.

19 Claims, No Drawings

AERIAL-SUPPORTED PROCEDURE FOR EXPLORATION OF HYDROCARBON DEPOSITS

BACKGROUND OF THE INVENTION

1. Technical Field

The present invention refers to an aerial-supported procedure for the exploration of hydrocarbon deposits, especially crude oil and gas deposits, using fluorescence procedures, including aerial-supported geo-referencing of the detected locations by means of a digital terrain model, employing biosensors which are sensitive to hydrocarbons.

2. Description of Related Art

It is known that natural deposits of hydrocarbons, such as crude oil and gas deposits, have some natural escape of liquid or gaseous hydrocarbons to the surface. One basically distinguishes here between so-called micro seeps and macro seeps.

Macro seeps are essentially understood as natural outflows of liquid crude oil to the surface. Macro seeps mostly occur with deposits close to the surface. Since the times of the ancient Greeks and Romans, such macro seeps have served to make crude oil products. Later on, such visually detectable macro seeps have been used as indicators for crude oil deposits, in order to determine the locations for promising oil drillings.

Micro seeps are defined as smallest traces of hydrocarbons in liquid or gaseous form which rise to the surface from especially even deeper located deposits. Such micro seeps preferably occur where the geological structures facilitate the buoyancy of light hydrocarbons in permeable rocks, filled with fresh or salt water. The occurrence of micro seeps is not limited to the presence of such geological structures. Thus, micro seeps are also generated by diffusion processes, especially the short-time hydrocarbons. Under ideal conditions of a homogenous rock, a micro seep has a circular configuration with an increasing hydrocarbon concentration towards the centre of the circle.

For the exploration of macro seeps or oil pollutions on the water which have the same effect as macro seeps, a variety of aerial-supported exploration and detection methods are known. As examples therefore, just the visual detection and the sensor supported detection by means of a radar with lateral viewer, microwave radiometers, infrared/ultraviolet scanners and laser sensors have been used in the past. However, to detect macros seeps, these methods require a large quantity of oil on the surface for their detection.

Methods of detecting micro seeps are known which make use of micro-organisms. For example, U.S. Pat. No. 2,777,799 describes a method for the geo-microbial prospection of oil deposits, making use of the fact that certain natural micro-organisms are using short-time hydrocarbon compounds as an energy source. According to the procedure proposed in this patent, soil samples are taken close to the surface and exposed under laboratory conditions to an atmosphere containing oxygen and $C^{14}$-marked hydrocarbons. After a sufficiently long incubation time, the metabolised $C^{14}$-content is measured, allowing conclusions on the content of natural micro-organisms metabolising the hydrocarbons in the sample. The content of natural micro-organisms metabolising the hydrocarbons allows conclusions on the natural content of hydrocarbons in the soil at the location where the sample was taken and therefore an indication on possible micro seeps. The proposed procedure, however, shows up considerable disadvantages. The procedure requires a great deal of effort which results in a limited number of analyses of samples and therefore in a rough sample pattern. Micro-organisms which can use hydrocarbon compounds as an energy source are known from the following publications: Manfred Wagner et al., "Microbial prospection on oil and gas in East Germany, Yearbook of Geology A 149, page 287-309, Hanover 1998; as well as Sorkhon et al. (1995) "Establishment of oil-degrading bacteria associated with cyano-bacteria in oil-polluted soil", *J. Appl. Bacteriol*, February; 78 (2): pp 194-9.

Moreover, it is known how to genetically manipulate appropriate micro-organisms in such a way that they produce fluorescence by means of a fluorescent protein when they absorb or come in contact with hydrocarbons. Respective processes for the manipulation of appropriate micro-organisms are state of the art in microbiology. So Figueira et al. (2000) describes such a bacterium in "Production of green fluorescent protein by methylotrophic bacterium extorquens"; *FEMS Microbiology Letters*, V 123, (2), pp. 195-200. Equally known are genetically manipulated micro-organisms, for example by Helinge, (2002) "Construction of fluorescent biosensor family"; Protein Science, pp. 2655-2875. However, heretofore, such biosensors have only been used in a laboratory setting and because sampling of a region is random, there is sporadic and limited information on the sampling area regarding the extent of deposits With a view to the increasing exploration of hydrocarbon deposits, there is an urgent need for further exploration methods, especially for exploration methods which detect the above-mentioned micro seeps without the negative aspects of the heretofore methods of detection.

SUMMARY OF THE INVENTION

The present invention provides for a method to overcome the disadvantages of the today's state of the art and to provide a procedure for the exploration of hydrocarbon deposits, especially for micro seeps related hereto, by using biosensors in combination with aerial examination of the area using high speed and precision detection methods.

In one aspect, the present invention provide for a method for detecting solid, liquid or gas hydrocarbon deposits in a testing area to be examined, the method comprising:

a) aerial spreading of biosensors on the surface of the testing area to be examined, wherein the biosensors have the ability to metabolize hydrocarbons and provide an indicator signal of such metabolism;

b) waiting a sufficient amount of time for interaction of the biosensors with the hydrocarbons for the metabolism of the hydrocarbons;

c) exposing the biosensors and surface of the testing area to an aerial-supported source of electromagnetic energy having at least one wavelength sufficient to stimulate the indicator signal of the biosensors;

d) detecting simultaneously the indicator signal of the biosensors and the surface reflection signal of the electromagnetic energy to provide data for a digital terrain model showing topographic detail of the surface testing area and locations of hydrocarbon deposits.

Another aspect of the present invention provides a method which allows the cartography of the locations through high-precision geo-referencing.

A still further aspect of the present invention provides topological data of geo-referenced area being examined.

Various other aspects, features and embodiments of the invention will be more fully apparent from the ensuing disclosure and appended claims.

DETAILED DESCRIPTION OF THE PRESENT INVENTION

The present invention provides a procedure to detect the locations of hydrocarbon deposits and especially of micro seeps from the air by means of aerial-supported laser scanners, in combination with biosensors sensitive to hydrocarbons, under simultaneous, high-precision geo-referencing, based on a digital terrain model.

The present invention makes use of the well-known biosensors which are sensitive to hydrocarbons on the basis of manipulated micro-organisms, hereafter just called biosensors. Appropriate biosensors include any micro-organism that can successfully metabolize hydrocarbon and provide an indicator of such metabolism. Further, any recombinant micro-organism that has been genetically manipulated to express green fluorescent protein in combination with the metabolism of hydrocarbons can be used in the present invention. For example, the micro-organism may include those described in by Figueira et al. (2000) "Production of green fluorescent protein by methylotrophic bacterium extorquens"; *FEMS Microbiology Letters*, V 123, (2), pp. 195-200.

As to the procedure according to the present invention, aqueous solutions of the cultures of the biosensors are spread out in a suitable process. A well-known possibility for a fast spread-out on a large surface makes use of sprayer airplanes which spread aerosol or mist of the aqueous solutions of the culture on the area which has to be examined.

This spreading of the micro-organism is followed by a reaction time during which the micro-organisms, serving as biosensors, interact with the hydrocarbons in or on the soil of the micro seeps that are to be detected. After a sufficient interaction time of the biosensors with the hydrocarbons they are activated and ready for detection.

In accordance with the present invention, the detection is executed by aerial-supported laser scanners, comprising at least one modified laser for the stimulation of a fluorescent radiation of the biosensors on the surface, in combination with the aerial-supported detection and geo-referencing of the fluorescent radiation by means of imaging processes of the laser scanner, as well as optionally, the representation of detailed field maps.

During the flight, an aerial-supported laser scanner is used in order to make a continuous altimetry of the flown over area which has to be surveyed. In a basically well known procedure, the individual elevation values are determined by the laser scanner, measuring the propagation time of the laser pulses which are reflected on the ground. At the same time, a precise geographic position of the airplane is attributed to each individual measured elevation value. The geographic position can be determined by DGPS (Differential Global Positioning System), especially in combination with precise inertial navigation equipment.

From the resulting elevation data, in combination with the corresponding position data, a digital terrain model of high resolution is generated which gives a precise image of the surface of the flown over area.

In a special embodiment it is possible to distinguish between the first and the last reflection on the ground of a multi-reflecting laser pulse between the ground surface on one hand and the upstanding vegetation or other artefact objects on the ground on the other hand. Hereafter the representation of the immediate ground surface is defined as digital ground model and the representation of the surface with vegetation and/or artefact objects is defined as digital surface model. In this embodiment of the invention it is possible to represent the ground profile, e.g. in wooded regions, without the representation of the disturbing vegetation.

In another embodiment, the above-mentioned aerial supported laser scanner is combined with a digital line camera. The resulting visual image of the flown over area is then combined or superposed with the digital ground model and/or the digital surface model. The application advantages are further explained below.

For transforming the digital altimetry model into the digital ground model and/or digital surface model, the measured data is assigned to a screen. The measured data consist of altimetry data which is related to the geographic data, as explained before. The screen line width of the resulting screen is an essential characteristic of the present invention. An appropriate screen line width, i.e. the horizontal resolution of the model is 0.25 meter. The usual screen line width of exploration procedures with sample testing, known in the market, generally varies between 100 and 1000 meters. The present invention therefore allows a much higher resolution for the detection of smaller micro seeps, as well as their structure, concentration and peak values.

Appropriate laser scanners to reach a horizontal resolution of 0.25 meter or less are available in the market. The laser scanner ALTM 3100® of the firm Optech, Canada and Litemapper 2800® of the firm IGI mbH, Germany are given as examples.

Besides the appropriate laser scanner, also the flight altitude and the flight speed of the laser scanner over the ground have an impact on the horizontal resolution. Amongst experts it is known, that when passing the aforementioned resolution of 0.25 meter or less, the resolution can be improved by reducing flight speed and/or flight altitude.

Another particularity of the present invention is to adjust the emission wave length of the laser to the stimulation wave length of the biosensors. This measure stimulates the biosensors and activates a detectable fluorescent transmission if they have been activated by the contact with hydrocarbons. This so-called secondary radiation is emitted in a wave length which is defined in accordance with the biosensors. Here the wavelength of the secondary radiation is not equal to the stimulation wavelength. Depending on the biosensors and thus depending on the chosen fluorophore, the secondary radiation has generally a 30 to 60 nm longer wavelength than the stimulation radiation. This has the advantage that for a laser pulse with a defined wavelength which corresponds with the stimulation radiation of the biosensor, two signals of different wavelengths will be received. The first signal, i.e. the reflection signal, has the same wavelength as the stimulation wavelength and, in the way as described before, serves for geo-referencing of the measuring point. The second signal has a longer wavelength and shows the presence of activated biosensors and thus indirectly indicates the presence of traces of hydrocarbons at the measuring point. As a consequence hereof only one stimulation signal of one wavelength is needed. The use of a second laser with another wavelength for the detection of the surface signal, i.e. of the reflection signal is not required and can be dropped.

In another embodiment laser pulses of different wavelengths can be used. Laser pulses of different wavelengths in the sense of the present invention are at least two laser pulses which are transmitted simultaneously or nearly simultaneously to a measuring point where one of the laser pulses has the stimulation wavelength of the biosensor and the other laser pulse incorporates a wavelength which differs from the first one and where the latter laser pulse continues serving to generate the surface signal. In this embodiment the wavelength of the biosensor signal and of the surface signal are more distant from each other. A bigger distance of the wavelengths of the signals to be detected facilitates the discrimination and therefore the detection.

In a further sub-embodiment of the embodiment described before, even several laser pulses with different wavelengths for the stimulation of the biosensors can be employed. The latter measure is useful, if at least two different biosensors are employed simultaneously that have different stimulation wavelengths.

If according to this sub-embodiment two biosensors with different stimulation wavelengths are being employed, three laser pulses with different wavelengths would be useful. Two of the laser pulses hereby serve to generate the fluorescent signal and the third one to generate the surface signal (reflection signal). Whenever more than two biosensors with different stimulation wavelengths are employed at the same time, this practice should be used accordingly.

The simultaneous employment of different biosensors and therefore of different stimulation wavelengths can serve to detect mixtures of hydrocarbons, which contain different hydrocarbons, as far as the biosensors are selective for the respective hydrocarbons.

The employment of different biosensors is an advantage for getting a first indication on the composition of the hydrocarbons. This again can provide indications on the qualities of the deposits. The simultaneous use of different biosensors can also be indicated, in order to compensate for some difference in the response of the micro-organisms. Referencing with at least two different signals, based on two different biosensors, leads to a higher accuracy of measurement.

According to the invention, the laser scanner is equipped with a detection unit which is able to detect and discriminate signals with different wavelengths. The detection unit has an appropriate wavelength-discriminating suppression filter which is able to perform the measurements in both the wavelength ranges, as described before, within sufficiently short time intervals.

In another embodiment the detection unit has two separate detectors which individually detect the respective, specific wavelength of the described signals.

In a further embodiment the laser scanner is provided with a separate laser stimulation for the biosensors, as well as with a separate detection device for the emission wavelength of the biosensors, i.e. of the fluorescence signal, which are both integrated on the platform of the laser scanner and thus are equally geo-referenced by the precision of the laser scanner.

The above-mentioned advantages are obvious. After injection of the area to be examined with the biosensors, both a geo-referencing can be performed and the deposits in this area, especially the micro seeps, can be identified immediately in a single measuring step, i.e. overflying the area. A further essential advantage consists in the fact, the present method avoid inconsistency in measurements with regard to the geographic position. The detected fluorescent signal is directly correlated with the geo-referenced reflection signal, so that the position in the digital ground model and/or the digital surface model is clearly defined.

However, more advantages result from the geo-referencing. In the field of the classical exploration, concerning the examination of the geological properties of the underground, it has been known for a long time that hydrocarbon deposits are preferably formed in so called tectonic traps. It is also known that the mentioned tectonic traps can trace to the soil surface, whereby this tracing can reach an elevation displacement in the surface region of some centimeters to a few decimeters. These so-formed surface structures, which are however difficult to be recognized, show the characteristics of different traps which, will be explained more in detail hereafter.

It has been the practice for long in the exploration of hydrocarbons to look for such surface structures with relief differences from some decimeters to some meters and to perform test drillings at the identified suspected surfaces. However, this method involves considerable disadvantages, since not each suspicious-looking surface structure correlates with a trap and also not every trap represents a hydrocarbon deposit. Therefore a considerable high amount of unsuccessful test drillings is required in order to be successful.

The methods of the present invention, not only indicate the deposits of micro seeps, but at the same time, due to the geo-referencing, correlate them with the surface structures. Thus the prospector is furnished in a new way with a combination of different information, i.e. the tracing structures on one hand and the size, location and number of micro seeps on the other hand, which leads to an improved detection of hydrocarbon deposits and provides for substantial conclusions on scope and type of these deposits.

In the case of anticlinal formations, as a rule it can be assumed, that the light peaks of the micro seeps mark the highest points of the trap and the orientation of a possible longitudinal axle of such a structure. This will be normally the case as well for horst structures or overthrusts In those cases, where obstructions, like dislocations or overthrusts define the structural formation of the deposit or the trap, it can be generally expected that these obstructions, due to increased permeability for hydrocarbons, will be marked equally well at the surface through the measured light peaks of the micro seeps.

The proposed procedure of the invention also shows essential advantages, even if no changes of the surface structure have occurred. As demonstrated earlier, the proposed procedure of the invention allows a large-scale, but narrow grid examination of a suspected area for micro seeps. Presence, size and distribution of the micro seeps in the examined area also give the prospector indications on the occurrence of so-called stratigraphical traps, i.e. trap types where changes in the lithology of the reservoir rock form the trap structure. In the same way as with the structural traps, as mentioned before, the micro seeps found at the surface show an image of the extension of the stratigraphical traps, mentioned before. The following types of traps can be counted to the stratigraphical traps: e.g. unconformity traps, dwindling slabs or lenses. Moreover changes of the porosity and/or permeability in the reservoir rocks, stratigraphical types of traps are normally not to be detectable by conventional examination methods and therefore were very difficult to be explored.

More advantages of the proposed procedure of the invention, as well as of the system, result from the further phases of the exploration. Hereafter, the obtained, digital ground model and/or digital surface model with the positions of the detected biosensors, which are shown herein, will be transferred to a data visualizing device. Hereby optionally, the visual image of the area, which was optionally obtained, can be combined and/or superposed with the ground model and/or with the surface model.

Through the represented data, the prospector is able with high security to determine the positions of the detected biosensors and consequently promising positions of hydrocarbon deposits. Moreover, the proposed procedure of the invention allows the transfer of the aforementioned data to a portable data visualizing device, e.g. a laptop. This results in an advantage that the prospector is guided safely and quickly to the places of the micro seeps, which were detected by the aerial-supported method, in order to continue the examinations on site with conventional procedures.

The prospector can safely move on the area by means of the ground model and/or surface model demonstrated on the portable data visualizing device, especially in combination with the optionally visual representation. The respective deposits of the detected biosensors can be taken from the representation.

Already the pure digital ground model reproduces the surface of the area with all the details and thus allows a safe orientation, independent from any coordinates. By a visual comparison between the digital ground model and the reality of the area, specific structures can be recognized, without any doubt, and can be put in a relationship to the positions of the deposits.

In addition to the ground model, the digital surface model identifies in detail the upstanding vegetation, as well as all the artificial objects. Amongst the vegetation, well recognizable reference objects are included, such as trees, hedges, as well as edges of forests. Amongst the artificial objects, i.e. artefact objects especially fences, individual pales, wall enclosures, houses, sheds, wells, all kind of masts, as well as semi-permanent objects facilitate the orientation in the area additionally.

That which is claimed is:

1. A method for detecting solid, liquid or gas hydrocarbon deposits in a testing area to be examined, the method comprising:

a) aerial spreading of biosensors on the surface of the testing area to be examined, wherein the biosensors have the ability to metabolize hydrocarbons and provide an indicator signal of such metabolism;

b) waiting a sufficient amount of time for interaction of the biosensors with the hydrocarbons for the metabolism of the hydrocarbons;

c) exposing the biosensors and surface of the testing area at a measuring point to an aerial-supported source of electromagnetic energy having at least one wavelength sufficient to stimulate the indicator signal of the biosensors;

d) detecting simultaneously at the measuring point the indicator signal of the biosensors and the surface reflection signal of the electromagnetic energy to provide data for a digital terrain model showing topographic detail of the surface testing area and locations of hydrocarbon deposits.

2. The method of claim 1, further comprising:

plotting of the data of the surface reflection signal with superposition of the fluorescence signal to provide a data visualization.

3. The method of claim 1, wherein the aerial-supported source of electromagnetic energy is at least one laser.

4. The method of claim 1, further comprising scanning the surface of the testing area with a camera or digital imaging system to provide a visualised image of the terrain.

5. The method of claim 4, wherein the visualized image is superposed into the digital terrain model.

6. The method of claim 1, wherein the biosensors are retained in an aqueous solution and spread in an aerosol or mist on the surface of the testing area.

7. The method of claim 6, wherein the biosensors retained in an aqueous solution is spread on the surface of the testing area by an airplane.

8. The method of claim 1, wherein the aerial-supported source of electromagnetic energy is maintained at a consistent altitude above the surface of the testing area.

9. The method of claim 1, wherein the detection is executed by aerial-supported laser scanners, comprising at least one modified laser for the stimulation of a fluorescent radiation of the biosensors on the surface, in combination with the aerial-supported detection and geo-referencing of the fluorescent radiation by means of imaging processes of the laser scanner.

10. The method of claim 1, where in the flight speed and/or flight altitude is sufficient to provide horizontal resolution of about 0.25 meter.

11. The method of claim 1, wherein electromagnetic energy at a single wavelength is used to stimulate the biosensors and wherein the received wavelength from the biosensors will be of a longer wavelength then the reflection signal from the surface thereby indicating the presence of activated biosensors and hydrocarbons at the measuring point.

12. The method of claim 3, wherein the electromagnetic energy is delivered in a continuous or pulse mode.

13. The method of claim 3, wherein at least two lasers are used and each delivers a different wavelength of electromagnetic energy to a measuring point.

14. The method of claim 13, wherein at least two different types of biosensors having different stimulating wavelengths are used and the at least two lasers are employed simultaneously to provide different stimulation wavelengths.

15. The method of claim 14, wherein the at least two different types of biosensors detect different hydrocarbons.

16. The method of claim 1, wherein an aerial-supported laser scanner emitting laser pulses at a specific wavelength is used in order to make a continuous altimetry of testing area to be examined.

17. The method of claim 16, wherein the propagation time of the laser pulses which are reflected on the ground are measured thereby providing a digital terrain model providing a data on the surface of the testing area.

18. The method of claim 17, wherein the first and the last reflection at a measured point provides data on the ground surface and any upstanding artefact objects on the ground, thereby providing representation of the ground surface and any vegetation and/or artefact objects rising above the surface.

19. The method of claim 1, wherein the indicator signal of the biosensors is a fluorescence signal.

* * * * *